United States Patent [19]
Carraher, Jr. et al.

[11] Patent Number: 5,840,760
[45] Date of Patent: Nov. 24, 1998

[54] **MATERIALS AND METHODS FOR CONTROLLING METHICILLIN-RESISTANT *STAPHYLOCOCCUS AUREUS* MICROBES**

[75] Inventors: Charles E. Carraher, Jr., Parkland; Cynthia Butler, Boca Raton, both of Fla.

[73] Assignee: Florida Atlantic University, Boca Raton, Fla.

[21] Appl. No.: 752,706

[22] Filed: Nov. 19, 1996

[51] Int. Cl.$^6$ ................................................. A61K 31/32
[52] U.S. Cl. ............................................................ 514/493
[58] Field of Search ............................................... 514/493

[56] References Cited

U.S. PATENT DOCUMENTS 2,626,953  1/1953  Mack et al. .................................. 528/9
5,043,463  8/1991  Carraher, Jr. et al. ..................... 556/88

OTHER PUBLICATIONS

Carraher, Jr., Charles E. and John D. Piersma (1973) "Modification of Poly(vinyl alcohol) through Reaction with Tin Reactants" Die Angewandte Makromolekulare Chemie 28:153–160.

*Primary Examiner*—Kevin E. Weddington
*Attorney, Agent, or Firm*—Saliwanchick, Llyod & Saliwanchik

[57] ABSTRACT

The subject invention concerns a novel process for controlling methicillin-resistant *Staphylococcus aureus* (MRSA) microbes. The process comprises the use of organostannane-modified poly(vinyl alcohol) and naturally occurring small and large oxygen and/or nitrogen containing compounds, also referred to herein as modified tin-containing polymer (MTP) materials, to control MRSA microbes.

18 Claims, No Drawings

MATERIALS AND METHODS FOR CONTROLLING METHICILLIN-RESISTANT *STAPHYLOCOCCUS AUREUS* MICROBES

BACKGROUND OF THE INVENTION

Methicillin is a widely used antibiotic in the medical field. Methicillin, a penicillin derivative, has been known and extensively used as an antimicrobial agent since the early 1960s. As with other antibiotics, the extensive use of methicillin creates a situation where resistant strains of pathogens may develop. In fact, methicillin resistant strains have emerged and pose a significant health problem.

For example, the development of *Staphylococcus aureus* which are resistant to methicillin poses a serious problem to those in the medical field. Such methicillin-resistant *Staphylococcus aureus* microbes (MRSA) present life-threatening situations in hospitals.

Infections often occur after a patient is hospitalized. These infections were not present or incubating at the time the patient was admitted. Nosocomial infections, infections not directly attributable to a patient's primary reason for hospitalization, are a major health hazard in our health care system. Besides putting the patient at increased risk, such infections add significantly to the cost of health care by increasing the length of stay in the hospital, as well as initiation of patient isolation procedures.

The most insidious microorganism involved in nosocomial infections is MRSA. This microorganism commonly colonizes those patients who are seriously ill and in high-risk areas such as intensive care and burn units. It can be carried in the anterior nares of otherwise healthy health-care givers and transferred to the patient during routine attendance at the patient's bedside.

MRSA are the leading cause of wound infection after surgery. They can also cause pneumonia and bloodstream infections. MRSA infections can be fatal unless effectively treated with antibiotics. Unfortunately, MRSA are resistant to all beta-lactam antibiotics, including the third generation cephalasporines. They are also resistant to tetracylines, sulfonamides and streptomycin. Caution must be exercised when dealing with a patient with MRSA including scrupulous disinfection of the room, bed and everything with which the patient comes in contact. MRSA is easily transmitted by hand to hand contact.

Vancomycin is currently the drug of choice for victims of MRSA. It must be administered by IV and the dosage monitored by laboratory analysis while the patient is being treated. Thus, the ability for newly-discovered materials to inhibit MRSA is significant to the prevention of nosocomial infection caused by MRSA.

U.S. Pat. No. 5,043,063 discloses and claims products based on poly (vinyl alcohols) (PVA) which have been modified with organostannane compounds. As disclosed in the patent, the compounds inhibit the growth of Candida microorganisms. Other microbes, such as *S. aureus* which are not resistant to methicillin, were inhibited to a much lesser degree. The modification of PVA has previously been reported. As early as 1973, the modification of PVA through reaction with specific organostannane halides was described (Carraher, C. and J. Piersman [1973] *DieAngewandte Makromolekulare Chemie*, 28:153). Polymeric organic tin compounds are also described in U.S. Pat. No. 2,626,953, issued to Mack et al. No biological activity was reported, or even suggested, by Carraher and Piersman for the organostannane polymers which they prepared or by Mack et al. in their patent for polymeric organic tin compounds though it is generally known that some tin-containing compounds may exhibit biological activity.

There is no disclosure or suggestion in U.S. Pat. No. 5,043,063 that the compounds disclosed therein might have activity against MRSA. There remains a great need to identify agents which have activity against MRSA.

BRIEF SUMMARY OF THE INVENTION

The subject invention concerns the use of tin-modified polymers to control methicillin-resistant *Staphyloccus aureus* microbes (MRSA).

In a specific embodiment, the compounds used in the methods of the subject invention are compounds that can be prepared by reacting polar functional groups with organostannanes. The bonding occurs through the polar function group and the organostannane. The compounds which can be reacted with organostannanes include natural and synthetic compounds. Natural materials include large and small carbohydrates and lignin. The carbohydrates may be relatively small molecules such as sucrose or larger molecules such as dextran or cellulose. Synthetic materials such as poly(vinyl alcohol), poly(acrylic acid) and poly(ethylene imine) can also be used. The organostannane moieties include both aromatic and aliphatic compounds as well as mixed organostannanes such as diethyltin, tripropyltin, methylhydrogentin, monomethyltin, and dibutyltin.

The process of controlling MRSA according to the subject invention can be carried out in various ways utilizing the teachings provided herein. These procedures will depend on the particular environment or medical setting where the MRSA are, or may present, a problem. For example, the modified tin-containing polymer (MTP) of the present invention can be impregnated into various articles to control and prevent outbreaks of MRSA thereon.

DETAILED DISCLOSURE OF THE INVENTION

The subject invention relates to the use of modified tin-containing polymers (MTP) to control methicillin resistant *Staphyloccus aureus* (MRSA). In the illustrated embodiments set forth herein, the MTP can be obtained from the chemical reaction of organotin halides (organostannane halides) with oxygen-containing or nitrogen-containing polymers. The modified polymers can be natural (for example, dextran, cellulose and lignin) or they can be synthetic such as poly(vinyl alcohol) (PVA) compounds. In addition, it is possible to manufacture a sucrose-based MTP through the reaction of sucrose with organotin halides even though the original sucrose is not polymeric.

The methyl-, ethyl-, propyl-, and butyl- compounds are preferred in the various embodiments of the present invention. Generally, the activity of the material is of the order of teriary (or tri-) which is greater than secondary (or di-) which is greater than primary (or mono-). Thus, the most active material (ranked in order of effectiveness) is derived from the reaction between the natural oxygen-containing polymer or poly(vinyl alcohol) with a tri-, di, and monoorganostannane halide such as chloride.

Using the methods described in U.S. Pat. No. 5,043,063 which is incorporated herein by reference, it is possible to effect the reaction of organostannane halides where the R groups may be methyl, ethyl, or propyl. Other R groups such as butyl and phenyl can also be prepared.

Compounds useful according to the subject invention may have, for example, one of the following structures if based on PVA.

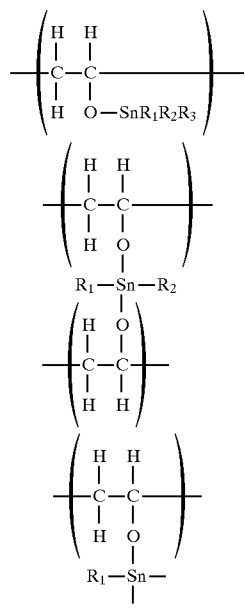

I

II

III $R_1$, $R_2$, and $R_3$ may be the same or different and may be hydrogen, methyl, ethyl, propyl, butyl, or phenyl. In an alternative embodiment the polymer may be a nitrogen containing polymer instead of an oxygen-containing polymer.

Additional antibiotic compounds useful according to the subject invention can be prepared from other initial compounds which contain a polar functional group. For example, antibiotic compounds useful according to the subject invention, based on lignin, include:

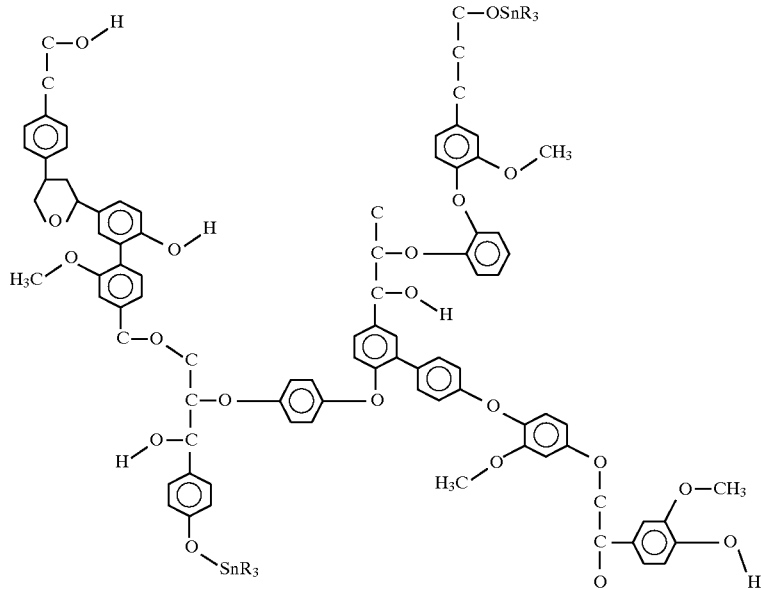

Antibiotic compounds can be made from dextran as follows:

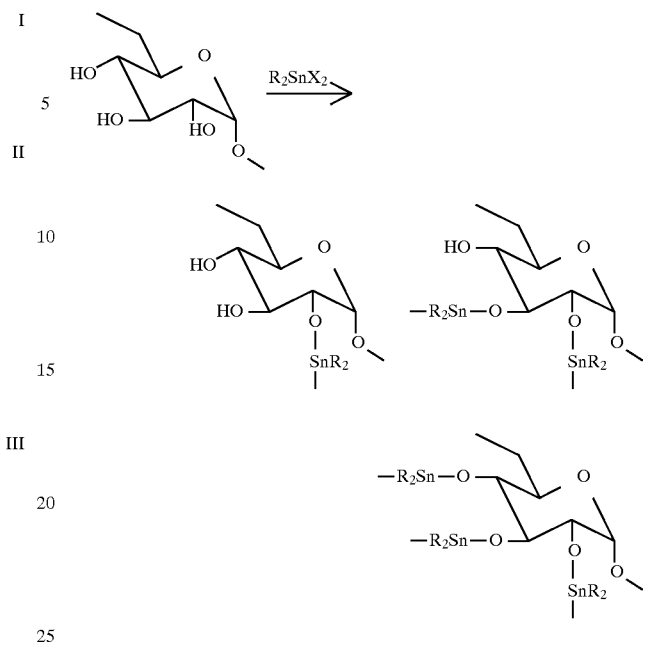

Antibiotic compounds can be made from cellulose as follows:

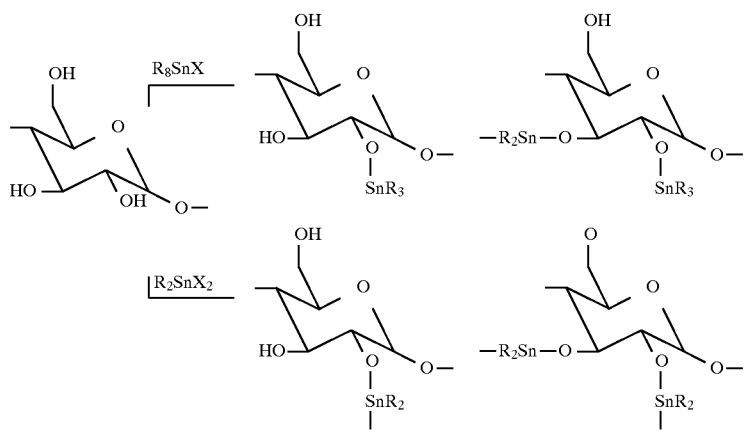
Antibiotic compounds can be made from sucrose as follows:
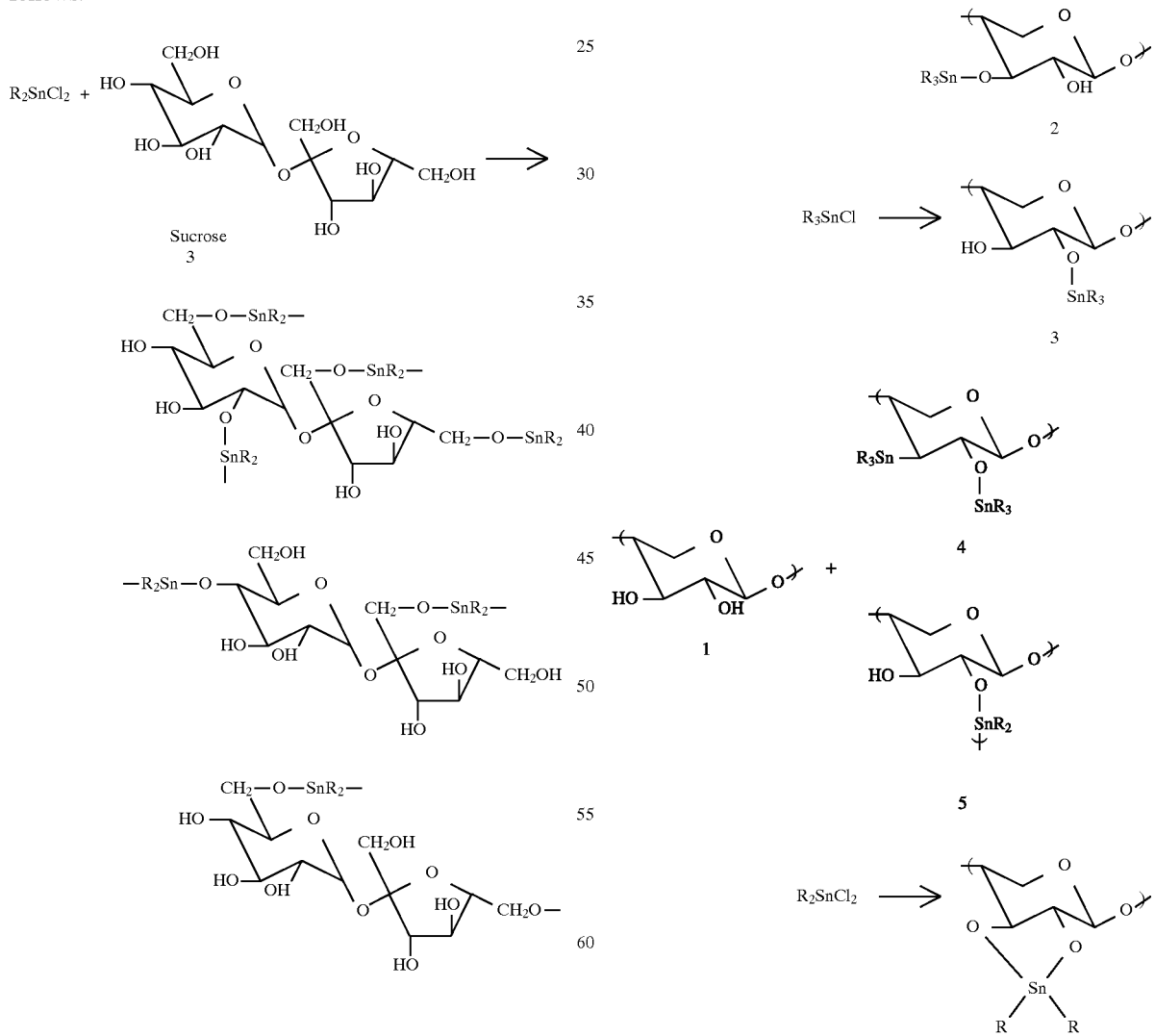
Antibiotic compounds can be made from xylan as follows:

-continued

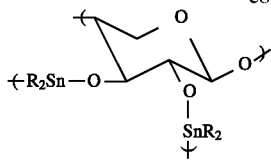

7

A synthetic nitrogen-containing compound of the subject invention may have the following formula:

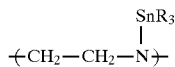

Compounds of the subject invention can also be based on natural nitrogen-containing compounds including, for example, chitosan, which contains both "OH" and "NH" reactive groups.

The compounds of the invention are useful for various non-therapeutic and therapeutic purposes. It is apparent from the testing that the compounds of the invention are effective for inhibiting MRSA. Because of the bateriocidal properties of the compounds, they are useful to swab hospital areas and equipment in a microbiology laboratory to eliminate the presence of microbes, either prior to or after microbe invasion. As disclosed herein, they are also useful prophylactically and therapeutically for treating microbial infections in animals and humans.

The compounds of the subject invention can be used in a variety of applications where microorganisms must be controlled. For example, these compounds can be incorporated into specialty paints, coatings, caulks, sealants, films, adhesives, grout, ceramics, cements, elastomers, plastics, powders, talc, or rubber latex where they will control microbes.

Also, because absorbent personal products and diapers are a fertile source for harboring MRSA, the MTP compounds can be impregnated into such entities to control these pathogens.

Therapeutic application of the new compounds and compositions containing them can be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the infection, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that an effective amount of the bioactive compounds(s) is combined with a suitable carrier in order to facilitate effective administration of the composition.

In a preferred embodiment, the MTP of the present invention can be impregnated into various articles to control and/or prevent outbreaks of MRSA thereon. For example, the MTP material can be impregnated into a variety of plastics, in latex coatings, powdered for addition to talc, cream or lotion based products or to paints, sealants or caulks. Tables 1 and 2 set forth experimental results of various MTP material compounds that can be used in the various embodiments of the present invention.

TABLE 1

Inhibition of MRSA by organostannane materials

| Products (*) | Inhibition MRSA-cm | Inhibition Normal-cm |
|---|---|---|
| Bu2Sn/PEG/Lignin | 0,0 | 0 |
| Bu2Sn/Lignin | 0,0 | 0 |
| Laury12Sn/Lignin | Contact | 0 |
| Bu3Sn/Lignin | 0.5, 0.6 | Contact |
| Bu2Sn/Si(2400)/Lignin | Contact | 0 |
| Bu2Sn/Si(1200)/Lignin | 0.1 | 0.3 |
| Laury12Sn/PEG/Lignin | 0 | 0 |
| Et2Sn/Dextran | 0.6, 0.4 | 1.0 |
| Et2Sn/Cellulose | Stasis | 0.6 |
| Et2Sn/Sucrose | Stasis | 0.5 |
| Pr3Sn/Cellulose | 1.3 | 2.0 (Stasality) |
| Pr2Sn/Sucrose | Contact | 0.4 |
| Bu2Sn (17%)/Dextran | 0.1 | Contact |
| Bu2Sn (20%)/Dextran | 0.2 | Contact |
| Bu2Sn (23%)/Dextran | 0.2 | Contact |
| Bu2Sn (26%)/Dextran | 0.1 | Contact |
| Bu2Sn/Cellulose | 0.5 | 0 |
| Laury12Sn (15%)/Dextran | 0 | 0 |
| Laury12Sn (32%)/Sucrose | 0 | 0 |
| Me2Sn (12%)/Dextran | 0.2, 0.2 | 0.4 |
| Me2Sn/Cellulose | Contact | 0.5 |
| Me2Sn (31%)/Sucrose | 0.8, 0.5 | 0.9 |
| Ph2Sn (34%)/Sucrose | 0.1 | 0 |
| Ph2Sn (12%)/Dextran | 0 | 0 |
| Oct2Sn/Cellulose | 0 | 0 |
| Cyclohex2Sn (23%)/Dextran | Contact | 0 |
| Ph3Sn (14%)/Dextran | 0.1, 0.5 | 0 |
| Ph3Sn/Cellulose | 0.3, 0.5 | 0 |
| Ph3Sn/Xylan | 1.0 | Contact | where Ph = phenyl, Me = methyl, Oct = n-octyl, Bu = butyl, Pr = n-propyl, Et = ethyl, PEG = hydroxyl-terminated poly (ethylene glycol), Si = hydroxyl terminated block copolymers composed of PEG-block with poly(dimethyl silane)-block with PEG and Si 1200 has the block with a molecular weight of 1200 Daltons and Si 2400 has a block with a molecular weight of 2400 Daltons.
(*) number in parentheses is the percent of tin incorporated in the product

TABLE 2

Inhibition results of MRSA by various organostannane-containing materials

| Product | Inhibition-cm |
|---|---|
| Pr2Sn/PVA | 0.5 |
| Ph3Sn/PVA | 0.3 |
| Ph3Sn/PVA | 2.5 |
| Me2Sn/PVA | 0 |

MATERIALS AND METHODS

Commercial PVA (99% hydrolyzed, Aldrich, Milwaukee, Wis.) was employed along with the organostannane halides (from Aldrich) as received. A variety of molecular weight PVAs are available and may be used according to the subject invention.

An aqueous solution of PVA containing sodium hydroxide can be used. The amount of sodium hydroxide may be, for example, equal to the theoretical maximum mole amount of chloride (or other halide) available from the organostannane halide. Stirring (about 18,000 rpm, no load) is begun and the organic solution (generally carbon tetrachloride or chloroform or other suitable organic liquid or mixtures of liquids) containing the organostannane halide added. Virtually any method of addition may be used. For example, the organostannane halide may be added rapidly at room temperature. The product rapidly precipitates from the reaction mixture, is collected by suction filtration, washed repeatedly with water, transferred to a glass petri dish and dried. When a plasticizer was used, it was added to the organic phase prior to the reaction. For example, 2 ml of a plasticizer could be used.

Thermogravimetric analysis was conducted employing a duPont TGA while differential scanning calorimetry was carried out using a duPont 900 DSC cell. Infrared spectra were obtained using films employing a Nicolet 5DX-FTIR. Mass spectral analysis was carried out by the Nebraska Mass Spectrometry Service Laboratory. Analysis was carried out using a direct insertion probe connected to a Kratos MS-50 mass spectrometer operating in the E.I. mode, 8 kr acceleration and 10 sec/decade scan rate with a probe temperature to 450° C.

Following are examples which illustrate procedures for practicing the invention. These examples should not be construed as limiting. All percentages are by weight and all solvent mixture proportions are by volume unless otherwise noted.

EXAMPLE 1

Process for Preparing MTP Materials

One procedure for preparing MTP materials is as follows: (1) dissolve 1 mole of tributyltin chloride in 50 ml. of organic solvent; (2) dissolve naturally occurring polymer (or monomer) in 50 ml. of water (equivalent to 1 mmole of hydroxide) with 1 mmole of a base such as sodium hydroxide; (3) combine and mix the tin and polymer reactants for between 15 and 60 seconds until the MTP material precipitates. The MTP material is then washed to remove unreacted tin-containing reactants and then dried.

EXAMPLE 2

Use of MTP Materials In Medical Tape To Control MRSA

MRSA poses a high risk to compromised patients, such as patients with open wounds, or patients who have undergone diagnostic and therapeutic procedures. Once present in such an environment, MRSA is attracted by static electricity to plastic surfaces such as IV lines which subsequently become sources of contamination to the patient coupled thereto. The present invention provides one means for eliminating such MRSA contamination. Specifically the MTP material of the present invention can be provided as tape segments and applied to one or more locations on an IV line (or other such article) whenever the IV line is changed or a new drip bag is hung.

Length of tape may have an adhesive layer deposited on a flexible mylar or plastic base layer. The adhesive layer may be either organic or inorganic. Selected organic adhesives, including cellulose adhesives such as methylcellulose and ethylcellulose or vegetable adhesives derived from processed starch such as the dextrins are compatible with the organostannane materials listed in Table 1 and may be advantageously substituted or blended with the above listed organic adhesives and applied as an improved layer 32 that will inhibit MRSA.

In the preferred tape embodiment, the polyvinyl alcohol compounds (PVA) listed in Table 2 are preferred for medical tape applications because such thermoplastic material has permanent solubility and fusibility so that the material will creep under stress and will soften when heated. Individual lengths of medical tape segments comprising one of the PVA compounds (collectively referred to as "PVA-MTP" hereafter) can be prepared as thin film strips and packaged in a manner similar to individual bandages (for example, an individual "BAND-AID"). When a new IV line is placed in a patient or when a new drip bag is coupled to the IV line, a plurality of such packages are warmed by the health care worker using, for example, their body heat, opened and applied to the IV line by stretching the PVA-MTP material around the IV line. Due to the tacky pliable and stretchy nature of the PVA-MTP material it will adhere in a semi-permanent manner as it cools yet be easily removable if necessary. With a plurality of segments applied to the IV line, the likelihood of MRSA is reduced. Further, if MRSA growth is present, the addition of a segment will eradicate such growth thereby reducing the likelihood of infection in the patient.

EXAMPLE 3

Use of MTP Materials In Detergents And Soaps To Control MRSA

Infections caused by MRSA micro-organisms as well as other pathogens can cause serious health care problems especially if a person's (or animal's) auto-immune response is weakened by AIDS or other illness. Accordingly, MRSA contaminated environments pose high risk to such patients. The present invention provides an economical means for the disinfection of the room, bed, linens, indeed everything a patient or employee might contact. The present embodiment of the invention is especially useful in high risk environments such as hospital emergency rooms, intensive care units and burn units.

As noted above, an entire room—its walls, tables, floors—may become so thoroughly saturated with MRSA that the physical setting serves as an amplifier contaminating subsequent patients who use the room. The present invention provides a economical means for quickly reducing or eliminating such MRSA contamination.

A selected composition of the MTP material is dried, crushed to a powder form and applied to detergent. The organic compounds (MTP) listed in Table 1 are preferred additives for detergent applications since such compounds are dispersible in water or other polar solvents. The detergent is preferably a cationic surfactant such as tallow trimethylammonium (p. 772 *Van Norstrand's Scientific Encyclopedia*, Fifth Edition). Because the tin in the MTP material is fully bound, there is no interaction between the tin and the surfactant nor does the tin interfere with the removal of soils or residue clinging to the surface to be cleaned. The MTP material will control any MRSA present. Advantageously, the MTP material can form a deposit on the cleaned surface thereby preventing reoccurrence of MRSA growth. As will be appreciated by one skilled in the art, the relative concentration of the MTP material in the detergent will vary depending on the chemical composition of the detergent, the presence of builders and the manner of application the only material criteria being that, during the washing process, substantially uniform distribution is obtained when a surface is swabbed leaving a dilute residue on the swabbed surfaces. Accordingly, only relatively small quantities of MTP material need be added to the detergent to obtain microbial growth inhibition.

This powder also can be added to liquid germicidal soap since MRSA is easily transmitted by hand to hand contact. In liquid soap, the MTP or PVA-MTP is held in colloidal suspension. In one preferred embodiment, between 3% and 20% and preferably about 5% by weight of the MTP is added to liquid soap.

EXAMPLE 4

Use of MTP Materials In Paints And/Or Plastics To Control MRSA

In other embodiments of the present invention, the MTP powder may be added to oil- or water-based paint either during the manufacturing process or thereafter during the color blending process. When applied to areas such as floors and walls having a high susceptibility for exposure to MRSA and similar organisms, the modified paint renders such surfaces inhospitable to MRSA or other microbes.

In yet another embodiment, the PVA-MTP is powdered and dispersed in melted plastic using well known manufacturing techniques. The melted plastic is then injected into a mold to form medical devices such, for example, syringes or IV tubes. Medical devices made from such PVA-MTP-containing plastic will create an inhospitable surface for MRSA notwithstanding the natural affinity MRSA has for plastic. In this manner, medical devices can be manufactured that will not serve as amplifiers in an otherwise MRSA contaminated environment.

EXAMPLE 5

Use of MTP Materials With Other Biologically Active Compounds To Control MRSA The MTP materials of the subject invention can be mixed with other biologically-active compounds in the above-identified preparations to control MRSA and other undesirable microbes. Materials such as antibiotics can be so employed. A person skilled in the art can, by routine experimentation determine the compatibility of other materials mixed with MTP materials to broaden the scope of microbe control.

The MTP materials disclosed in U.S. Pat. No. 5,043,063 can be used in the process of the subject invention. Thus, the disclosure of such materials and their preparation in U.S. Pat. No. 5,043,063 is incorporated herein by reference thereto.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A process for controlling methicillin-resistant *Staphyloccus aureus* (MRSA) microbes which comprises contacting said MRSA with an effective anti-MRSA amount of a modified tin-containing material.

2. The process, according to claim 1, wherein said MTP material can be shown by the following structural formula:

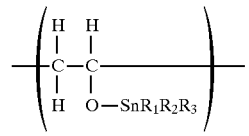

wherein $R_1$, $R_2$, and $R_3$ may be the same or different and are selected from the group consisting of methy, ethyl, propyl, butyl, and phenyl.

3. The process, according to claim 2, wherein $R_1$, $R_2$, and $R_3$ are methyl.

4. The process, according to claim 2, wherein $R_1$, $R_2$, and $R_3$ are ethyl.

5. The process, according to claim 2, wherein $R_1$, $R_2$, and $R_3$ are propyl.

6. The process, according to claim 2, wherein $R_1$, $R_2$, and $R_3$ are butyl.

7. The process, according to claim 1, wherein said MTP material can be shown by the following structural formula:

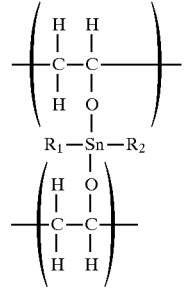

wherein $R_1$ and $R_2$ may be the same or different and are selected from the group consisting of methyl, ethyl, propyl, butyl, and phenyl.

8. The process, according to claim 7, wherein $R_1$ and $R_2$ are methyl.

9. The process, according to claim 7, wherein $R_1$ and $R_2$ are ethyl.

10. The process, according to claim 7, wherein $R_1$ and $R_2$ are propyl.

11. The process, according to claim 7, wherein $R_1$ and $R_2$ are butyl.

12. The process, according to claim 1, wherein said MTP material has the following structure:

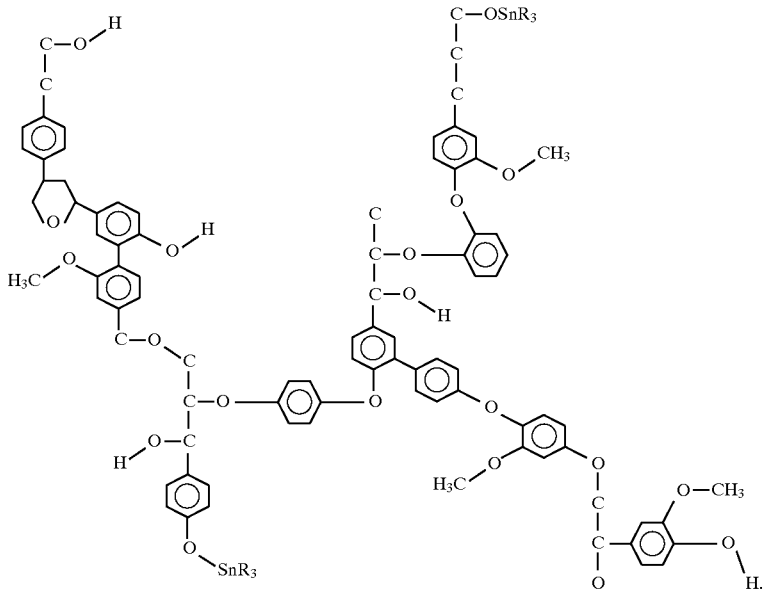

13. The process, according to claim 1, wherein said MTP material is a tin-modified compound wherein the compound which is modified is selected from the group consisting of dextran, cellulose, sucrose, and xylan.

14. The process, according to claim 1, wherein said MTP material has the following structure:

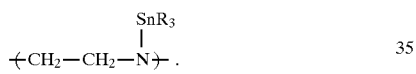

15. An article of manufacture comprising a modified tin-containing polymer (MTP) material.

16. The article of manufacture, according to claim 15, wherein said MTP material has the following structural formula:

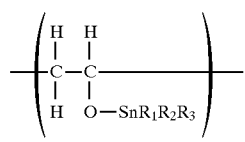

wherein $R_1$, $R_2$, and $R_3$ may be the same or different and are selected from the group consisting of methy, ethyl, propyl, butyl, and phenyl.

17. The article of manufacture, according to claim 15, wherein said MTP material has the following structural formula:

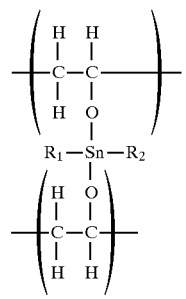

wherein $R_1$ and $R_2$ may be the same or different and are selected from the group consisting of methyl, ethyl, propyl, butyl, and phenyl.

18. The article of manufacture, according to claim 15, selected from the group consisting of medical tapes, detergents, soaps, paints, coatings, caulks, sealants, elastomers, powders, and plastics.

* * * * *

UNITED STATES PATENT AND TRADEMARK OFFICE
CERTIFICATE OF CORRECTION

PATENT NO.  : 5,840,760

DATED       : November 24, 1998

INVENTOR(S) : Charles E. Carraher, Jr., Cynthia Butler

It is certified that error appears in the above-identified patent and that said Letters Patent is hereby corrected as shown below:

Column 3, bottom structure:

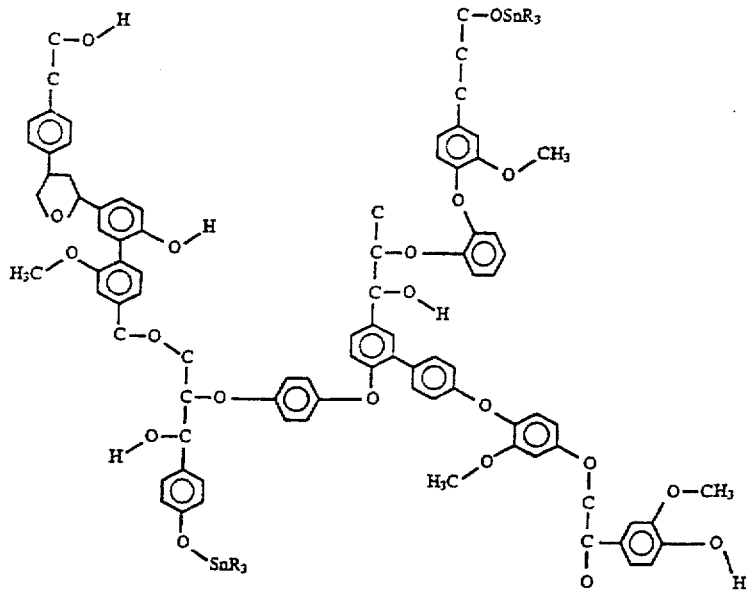

UNITED STATES PATENT AND TRADEMARK OFFICE
CERTIFICATE OF CORRECTION

PATENT NO.   :   5,840,760

DATED        :   November 24, 1998

INVENTOR(S)  :   Charles E. Carraher, Jr., Cynthia Butler

It is certified that error appears in the above-identified patent and that said Letters Patent is hereby corrected as shown below:

should read:

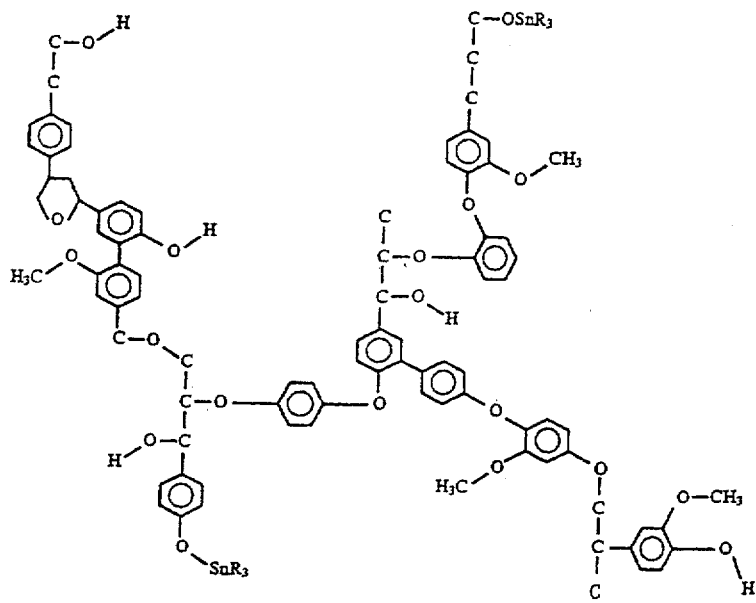

UNITED STATES PATENT AND TRADEMARK OFFICE
CERTIFICATE OF CORRECTION

PATENT NO.    :   5,840,760

DATED         :   November 24, 1998

INVENTOR(S)   :   Charles E. Carraher, Jr., Cynthia Butler

It is certified that error appears in the above-identified patent and that said Letters Patent is hereby corrected as shown below:

Column 13, top structure:

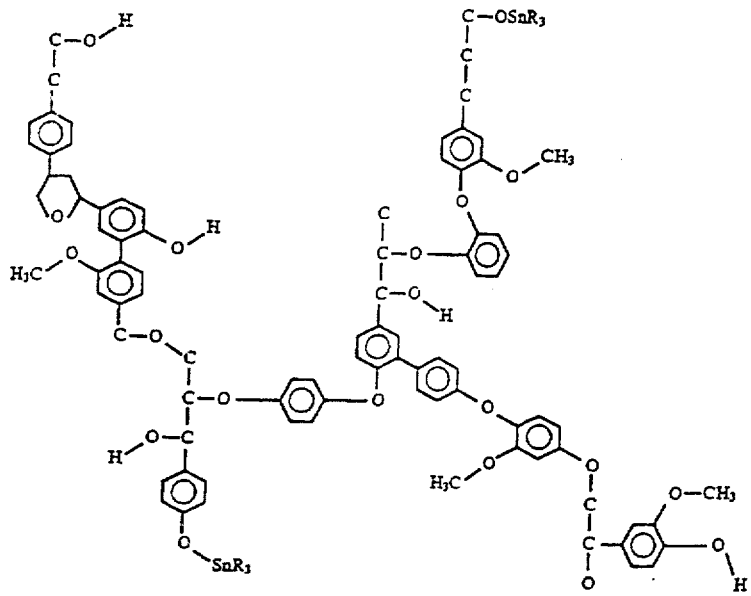

UNITED STATES PATENT AND TRADEMARK OFFICE
CERTIFICATE OF CORRECTION

PATENT NO.   :   5,840,760

DATED        :   November 24, 1998

INVENTOR(S)  :   Charles E. Carraher, Jr., Cynthia Butler

It is certified that error appears in the above-identified patent and that said Letters Patent is hereby corrected as shown below:

should read:

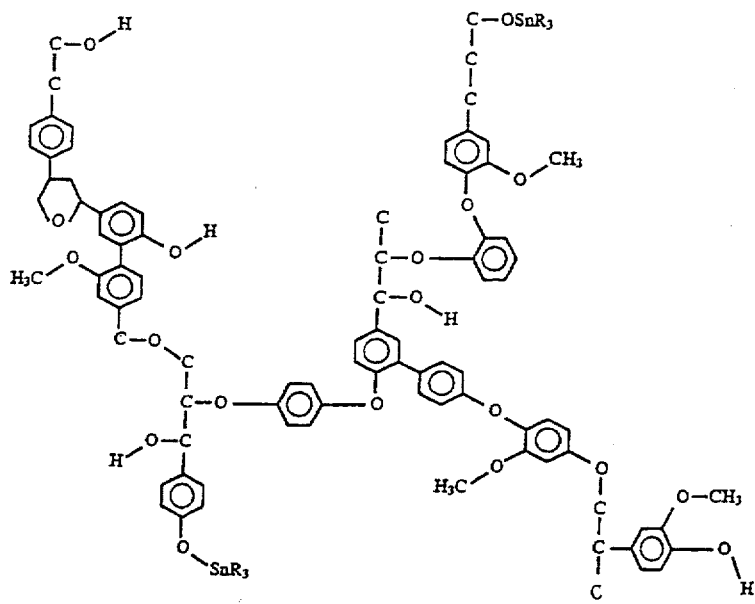

UNITED STATES PATENT AND TRADEMARK OFFICE
CERTIFICATE OF CORRECTION

PATENT NO. : 5,840,760

DATED : November 24, 1998

INVENTOR(S) : Charles E. Carraher, Jr., Cynthia Butler

It is certified that error appears in the above-identified patent and that said Letters Patent is hereby corrected as shown below:

should read:

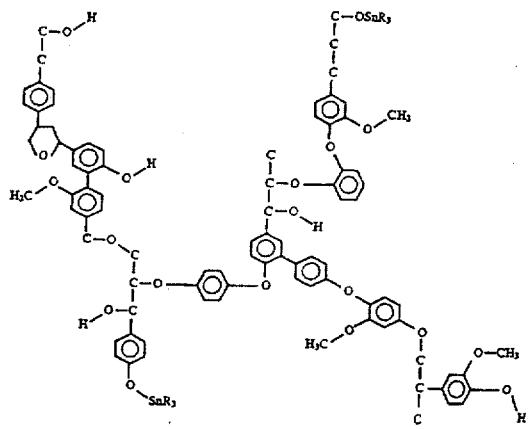

Signed and Sealed this

Twenty-third Day of March, 1999

Attest:

Q. TODD DICKINSON

Attesting Officer

Acting Commissioner of Patents and Trademarks